United States Patent [19]

Bradwell

[11] Patent Number: 5,429,951
[45] Date of Patent: Jul. 4, 1995

[54] RADIAL IMMUNODIFFUSION AND LIKE TECHNIQUES

[76] Inventor: Arthur R. Bradwell, 97 Vincent Drive, Edgbaston, Birmingham, B15 2SQ, England, B15 2SQ

[21] Appl. No.: 768,686
[22] PCT Filed: Apr. 26, 1990
[86] PCT No.: PCT/GB90/00655
 § 371 Date: Oct. 9, 1991
 § 102(e) Date: Oct. 9, 1991
[87] PCT Pub. No.: WO90/13031
 PCT Pub. Date: Nov. 1, 1990

[30] Foreign Application Priority Data

Apr. 26, 1989 [GB] United Kingdom ............... 8909478

[51] Int. Cl.⁶ ............... G01N 33/559; G01N 33/543; G01N 33/553; G01N 21/82
[52] U.S. Cl. ............... 436/515; 436/514; 436/518; 436/525; 436/534; 436/823; 422/57
[58] Field of Search ............... 436/515, 516, 513, 823, 436/514, 518, 525, 534; 514/23; 422/56, 57

[56] References Cited

U.S. PATENT DOCUMENTS

| | | | |
|---|---|---|---|
| 3,892,841 | 7/1975 | Barg, Jr. | 424/12 |
| 3,905,767 | 9/1975 | Morris et al. | 23/230 B |
| 3,966,897 | 6/1976 | Renn et al. | 436/515 |
| 4,169,138 | 9/1979 | Jonsson | 436/524 |
| 4,200,508 | 3/1980 | Hirai | 204/182.8 |
| 4,313,734 | 2/1982 | Leuvering | 436/525 |

FOREIGN PATENT DOCUMENTS

| | | |
|---|---|---|
| 250137 | 12/1987 | European Pat. Off. . |
| 1362776 | 7/1970 | United Kingdom . |
| 2204398 | 11/1988 | United Kingdom ...... G01N 33/532 |

OTHER PUBLICATIONS

Development and validation of a particle-enhanced turbidmetric immunoassay for C-reactive protein; Price et al; Jo Immunol methods, 99 (1987) 205–211.

Dunbar, B., pp. 143–150, From "Two-dimensional electrophoresis & immunol. techq." Plenum Press N.Y. 1987.

Haaheim, Reactivity of Rabbit . . . Immunodiffusion, Biosis, vol. 62, Abstr. No. 62066725 (1976).

Mancini et al., Immunochemical Quantitation . . . Immunodiffusion, Immunochemistry, vol. 2, pp. 236–238, 250–254 (1965).

Schall, Jr., et al., Alternatives to Radioimmunoassay: Labels and Methods, Clinical Chemistry, vol. 27, No. 7, pp. 1160 & 1161 (1981).

*Primary Examiner*—Michael P. Woodward
*Attorney, Agent, or Firm*—Baker, Maxham, Jester & Meador

[57] ABSTRACT

In a known method of immunodiffusion, a sample containing a first agent such as an antigen is introduced into a well in a lamina of agarose gel containing a second agent such as a complementary antibody. The first agent diffuses through the gel and becomes releasably bound to the second agent and, when the concentrations of agents are optimal, the agents form an extended matrix incorporating light-scattering aggregates. The size of the visible matrix enables the concentration of one of the agents to be assessed when that of the other agent is known. Each aggregate comprises very large numbers of the molecules of the agents. The invention provides an improved method in which the second agent is attached to carrier means in the gel so that the carrier means constitutes part of the visible aggregations. The carrier means may constitute the gel itself and/or it may constitute particulate material such as polystyrene particles.

21 Claims, 1 Drawing Sheet

U.S. Patent July 4, 1995 5,429,951
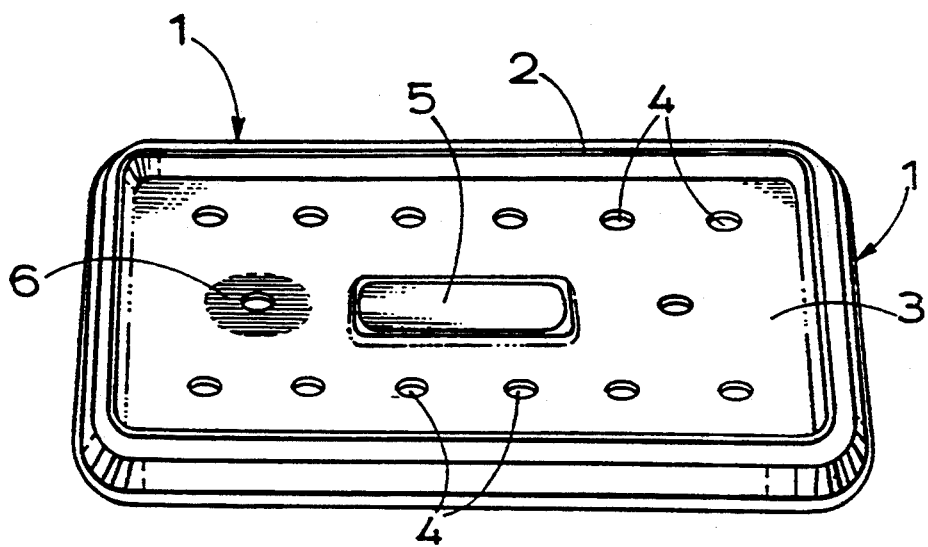

RADIAL IMMUNODIFFUSION AND LIKE TECHNIQUES

This invention is concerned with improvements in and relating to radial immunodiffusion and like techniques.

Several methods of measuring the concentration of a proteinaceous antigen in a sample are already known. A first of these methods is well-known and widely used and is normally referred to as immunodiffusion. In that method a sample of the material at a predetermined dilution is introduced into a well in a plate of agarose gel containing an antibody specific to that antigen, the antibody being present at a predetermined concentration in the gel. The sample diffuses radially from the well into the gel, where the antigen becomes releasably bound to the antibody. This results in the formation of a matrix which is visible as a ring, or sometimes as a disc, concentric with the well. With the passage of time the diameter of the ring or disc increases until a maximum diameter is reached, and it is usual for the inner part of the ring or disc to become less distinct or to disappear as the maximum outer diameter is reached. Experiment has shown that the concentration of antigen in the original sample is directly proportional to the maximum diameter of the ring or disc. The method is described in the following paper: Mancini G., Carbonara A. O. and Heremans J. F., *Immunochemistry*, 2, 235 (1965).

In a converse of that first method, which is of use in assessing the concentration of antibody in a sample, the agarose gel contains a predetermined concentration of the antigen, while the sample contains an unknown concentration of the complementary antibody.

The visible matrix is most clearly formed when the concentrations of the protein and the antibody are optimal. At those optimal concentrations most of the antibodies become bound to two separate molecules of antigen while most of the antigen molecules become bound to two or more separate antibodies so that extended aggregations of molecules are formed, those aggregations constituting the visible basis of the matrix. Where there is an excess of antibodies few or none of the antibodies are able to link together separate antigen molecules. Likewise where there is an excess of antigen molecules, some pairs of antigen molecules may each be linked together by an antibody molecule but those linked pairs are not linked to form large visible complexes as insufficient antibody molecules are present.

For a matrix to interfere with the direct passage of light through a gel, it must comprise individual aggregations of molecules each of which is of an extent which is at least about one twentieth of the wavelength of the light. In practice, noticeable scattering occurs when there are aggregations each of which is some 200 to 400 nm in diameter. As an individual antibody molecule or a typical individual antigen molecule is only a few nm across, e.g. about 5 to 8 nm across, it means that no scattering of light that is visible to the eye occurs until there are formed aggregations of molecules each consisting of a very large number of molecules, typically at least a few million molecules. It also means that the concentration of antibody and antigen molecules in the interstices of the gel is relatively high. This in turn presupposes an adequate concentration of the antibody (or conversely of the antigen) in the gel initially.

While that type of method of radial immunodiffusion is extremely valuable for some purposes it does nevertheless suffer from the drawback that its sensitivity is limited owing to the need to enable relatively large aggregations of molecules to be formed. Moreover, the method is slow at low concentrations.

A second known method of measuring the concentration of proteinaceous antigen in a sample makes use of a liquid reagent comprising a suspension of latex particles coated with antibodies. The particles are sufficiently small that their presence does not greatly reduce the clarity of the reagent. In use, however, when a proteinaceous antigen is added to the reagent, the antigen links some of the coated particles together so that aggregations are formed which noticeably reduce the clarity. The concentration of the antigen can be determined from measurements of the resultant opacity of the reagent. While this method can be carried out relatively rapidly and can be made more sensitive than the first method described above, it requires the use of relatively complex and expensive apparatus to provide accurate measurements of opacity.

The present invention provides, among other things, a modification of the existing methods which can avoid or reduce at least some of the difficulties associated with those methods.

From a first aspect the present invention consists in a method of detecting the presence of the first of a pair of complementary matrix-forming agents in a sample, in which method the sample is applied to a test body comprising a gel in which there is present the second of said pair of complementary matrix-forming agents, said second agent being attached to carrier means, allowing said first agent (if present) to diffuse through the gel until it is incorporated in a light-scattering matrix, the light-scattering properties of the matrix differing from those of the test body, and using a change in the light-scattering resulting from the formation ;of the matrix to detect the presence of the matrix and consequently the presence of said first agent in the sample.

The matrix is referred to above as being a light-scattering matrix, and it is this property that enables the presence of the matrix to be sensed and can also conveniently be used in determining its extent. While the light-scattering effect may be sensed visually by simple human observation, it may alternatively be sensed by inanimate sensing means such as by a device incorporating a light-sensitive detector. Moreover, although it is envisaged that the light of which the scattering is sensed would normally be in the visible spectrum this is not necessarily so, and it is within the scope of the invention to use a method in which the light of which the scattering is sensed is outside the visible spectrum; for example, it may be in the ultraviolet part of the spectrum.

From a second aspect the present invention consists in a test body for use in carrying out a method in accordance with the first aspect of the present invention and comprising a gel in which there is present said second matrix-forming agent attached to carrier means.

The carrier means may comprise the gel itself, the second matrix-forming agent being attached to the gel. Alternatively or in addition the carrier means may comprise particulate material.

The test body preferably resembles a test body of the kind used in carrying out the known method described above. That is, the test body is conveniently in the form of a lamina. This is preferably formed with a hole or "well" into which a sample is or can be introduced. The lamina is preferably of uniform thickness so that the volume of the matrix formed can be assessed by measuring its surface area or by measuring its diameter or radius if it is of circular configuration.

Nevertheless it is to be understood that while the invention may well employ gels in the form of laminae into which the sample is allowed to diffuse radially, it may employ gels of other shapes. For example a sample may be caused to diffuse along a narrow strip or column of gel.

The invention is based on the discovery that useful results can follow when said second agent is attached to carrier means. Before that discovery was made it had been thought that no such results could arise from that.

In particular it had previously been thought that a necessary requirement for the successful formation of a matrix in a gel was that both of the matrix-forming agents should be free to diffuse through the interstices of the gel. It had therefore been assumed that attaching the second matrix-forming agent to carrier means would interfere with matrix-formation or would wholly prevent matrix-formation. It has now been found that this is not so and that matrices can readily form even if said second agent is attached to carrier means and is therefore rendered less capable or even substantially incapable or wholly incapable of diffusing through the interstices of the gel.

It will be appreciated that when a particulate carrier material is used, that material constitutes part of any finally-produced light-scattering aggregation and that the concentration of matrix-forming agents in the aggregation is less than that which occurs in an aggregation of similar size incorporating no carrier material. Consequently, the second of the known methods described above can usually be carried out with samples that are less concentrated than those needed for carrying out the first of those known methods. In other words, the use of a particulate carrier can lead to an increase in sensitivity. On the other hand, as indicated above, it was expected that the use of a particulate carrier in a gel rather than a free liquid would not lead to matrix-formation or at least would not lead to satisfactory matrix-formation in view of the fact that the particles of the carrier would be prevented from moving in the gel or would be hampered in their movement.

In fact, however, the use of a particulate carrier in a gel can yield useful results. It is postulated that the seasons for this are as follows. First, it will be appreciated that in carrying out the first of the known methods, any visible aggregation requires there to be a relatively large concentration of linkages between antigen and antibody molecules, whereas in carrying out the second of the known methods, in which the aggregation incorporates a particulate carrier, the concentration of such linkages is less. Moreover, as the particle-size increases, the concentration of linkages in a visible aggregation is progressively reduced. It is suggested that when relatively small particles are employed mobility or those particles is only partially hampered by the gel and that the consequent reduction in speed of matrix-formation is at least partially counterbalanced by the reduction in the concentration of linkages required. When relatively large particles are used, they may be largely or wholly prevented by their size from diffusing through the gel. Nevertheless it appears that component strands of the gel are sufficiently flexible to enable neighbouring particles to approach one another sufficiently closely to enable the matrix-forming agent attached to those particles to become linked to the complementary agent diffusing through the gel. Thus it seems likely that the decreasing mobility that arises with increasing particle-size is adequately counterbalanced by the reduction in the concentration of linkages required in matrix-formation and the unexpected flexibility of the component strands of the gel.

Similarly, when the carrier means is constituted by the gel itself, the light-scattering aggregations that are formed incorporate portions of the gel. In order to increase the sensitivity of the method, use may be made of a gel with relatively thick component strands; a latex gel with relatively thick component strands may be suitable.

Another way of considering the advantages of the present invention is to compare two methods which differ from each other only in this, namely that in the first method the second agent is free in the gel, in a manner characteristic of the first of the known methods, while in the second method the second agent is attached to carrier means, in the manner characteristic of the present invention. The concentration of the second agent is the same in both methods and the concentration of the first agent in the sample is the same in both methods. When the samples are applied, matrix-formation occurs in the two gels at substantially the same rate but in the first method visible aggregations are formed more slowly than in the second method. Indeed, if the concentrations of agents are low, visible aggregations may not be formed at all in the first method. Consequently, use of the second method, in accordance with the invention, enables greater sensitivity to be achieved at low concentrations of agents and at higher concentrations enables readings to be obtained more rapidly.

A method in accordance with the present invention may be used not only for detecting the presence of said first matrix-forming agent but also for assessing the quantity of the first agent in the sample, this being done by providing initially a known concentration of said second agent in the gel and by determining the extent of the matrix when it has ceased to increase in size. When the test body is in the form of a lamina with a hole or well in it into which a sample of predetermined volume is introduced, the quantity of the first agent in the sample is proportional to the diameter of the ring or disc formed around the hole. If, on the other hand the test body is in the shape of a narrow strip or column, the quantity of the first agent in the column is proportional to the length of the visible matrix formed in the strip or column.

Conversely a method in accordance with the present invention may be used in calibrating the concentration of said second agent in a gel. To this end, use is made of a sample containing a known concentration of said first agent.

One of the complementary matrix-forming agents is preferably an antibody, the other agent being an antigen. The antibody preferably constitutes said second agent and is initially present in the gel.

As is well known, antigens become releasably bound to antibodies by a mechanism such that the association constant is considerably greater than the dissociation constant. Consequently, the rate at which a matrix forms is largely dependant on the value of the dissociation constant. In the formation of a matrix incorporating all or substantially all of the available molecules of said first agent, the first agent diffuses through the gel and becomes repeatedly bound to and released from said second agent until a matrix is formed.

It is found that for the present invention to operate satisfactorily the association Constant must be relatively high, and it is thought that this is a consequence of the fact that the binding forces between the agents must be great enough to resist the elastic forces exerted by the component strands of the gel which may tend to urge the agents apart. Whether or not any particular pair of complementary agents can be used in carrying out a method in accordance with the present invention can best be determined by experiment. As indicated above, antibodies and proteinaceous antigens can generally be employed satisfactorily. In general it is considered that for satisfactory operation the association constant should be relatively high, for example the equilibrium constant $K_{eq}$ should normally be at least $10^8$ moles$^{-1}$.

A method in accordance with the present invention may employ antibodies and proteinaceous antigens as complementary agents. Alternatively it may employ any of a wide range of other complementary agents. For example one of the agents may be avidin and the other agent biotin. Either one may constitute said first agent but in a preferred method biotin would constitute the first agent and avidin would constitute the second agent and be attached to a particulate carrier. Other complementary agents that may be employed are lectin and carbohydrates, particularly sugars. In a preferred method lectin constitutes the second agent, being attached to a particulate carrier in the gel, while the carbohydrate constitutes the first agent.

Turning now to the nature of the matrices that are formed when employing the first of the known methods and when employing the present invention, it has been observed that in general, when the first of the known methods is employed, a visible disc is first formed; its diameter progressively increases to a maximum but at the same time an inner part of the disc progressively disappears again so that the final visible matrix is in the shape of a ring. This is thought to be a consequence of the fact that both constituent agents can diffuse through the gel. In contrast, when the present invention is employed, the matrix generally forms a visible disc of which the inner part does not disappear. This is thought to result from the fact that the second agent is generally immobile or substantially immobile in the gel.

In its passage through the gel towards the rim of the ring or disc a molecule of said first agent is likely to become bound to and released from a large number of molecules of said second agent and to follow a non-rectilinear path, its gradual, overall movement occurring as a result only of the concentration gradient in the gel. In carrying out a method in accordance with the first known method referred to above, a great number of linkages must be formed before visible aggregations are formed so the method is relatively slow. In using a method in accordance with the present invention, however, the concentration of mutually bound agents necessary to yield a visible aggregation is reduced, owing to the presence of the carrier means, with the consequence that results can generally be obtained more rapidly.

When the carrier means is of particulate form it comprises a plurality of minute particles to each of which is attached a plurality of the molecules of said second agent. The particles may be particles of a latex such as a polystyrene latex. The manufacture of colloidal polystyrene particles coated with antibody molecules is already a known technique as such coated particles are used in the second of the known methods referred to above. Coated particles of that existing kind may also be used in gels embodying the present invention. Alternatively the particles may comprise a metal such as gold. Both polystyrene particles and gold particles are such that when they form part of an aggregation of the kind described they are relatively transparent. The matrices of which they form a part are visible because light is refracted and internally reflected by the constituent particles. Use of inherently more opaque substances may increase the visibility of the matrices. For example, use may be made of a carrier comprising particles each of which comprises a core of iron and a coating of polystyrene.

Whatever the nature of the particles, the surface of each particle normally carries a large number of molecules of said second matrix-forming agent, the overall concentration of that agent in the gel may therefore still be relatively high so that the concentration of said first agent necessary for the relative concentrations of the agents to become optimal will also be correspondingly high. Consequently the rate of formation of the completed matrix is likely to be relatively slow though visible aggregations may start to appear relatively quickly. However, by reducing the number of molecules of said second agent on the surface of each particle, while retaining the same concentration of particles, the overall concentration of that second agent in the gel is reduced so that the concentration of said first agent necessary for the relative concentrations of the agents to be optimal is also reduced. Consequently the sensitivity of the method is increased and the rate of completion of the matrix is also reduced. The size of the particles is such that even when molecules of said other agent are attached to them they are too small to scatter light of the wave-length used. Nevertheless, they may be of a size such that only a relatively few particles, for example fewer than five particles, when linked together form an aggregation large enough to scatter the light. Typically, particles may be used that have a diameter of about 100 nm though particles of other diameters may be used.

The accompanying drawing is a perspective view of one particular form of test plate for use in carrying out a method in accordance with the present invention, this being illustrated merely by way of example.

The test plate comprises a rigid tray 1 with a flat base in the shape of a rectangle with rounded corners and an upstanding peripheral flange 2. The tray carries a lamina 3 of uniform thickness constituting a test body in accordance with the present invention. An array of through holes 4 is formed in the lamina, as illustrated.

The lamina 3 comprises a gel incorporating polystyrene particles coated with antibodies. The particles are of uniform size, each typically having a diameter of 100 nm. Such polystyrene particles are available on the market and are usually supplied in an aqueous suspension containing 50% solids and at a relatively high pH, typically 9.5. When the particles are to be coated the suspension is diluted and subjected to ultrasonic radiation to ensure that the particles are fully separated from each other. A solution containing the desired antibodies is introduced, and the antibodies attach themselves to the particles, this occuring naturally as both the antibodies and the particles are hydrophobic. This action may be assisted if desired by the addition of a relatively small amount of albumin.

The lamina is formed from an agarose gel with a relatively long chain-length. This is heated to cause it to melt, melting usually occuring at about 100° C. The melted agarose is then cooled in controlled conditions, the agarose having the property that it does not solidify again until it reaches about 40° C. The coated particles are introduced into the liquid agarose when it is at a temperature above its melting point but below 56° C., at which temperature the antibodies would start to become damaged. When the particles have been thoroughly mixed with the liquid, the mixture is poured into the tray 1 and allowed to set to form a lamina of uniform thickness. After it has set the lamina is temporarily removed from the tray and the holes 4 are punched through it before it is returned to the tray. An identification label 5 is attached to the gel.

In use a predetermined volume of a liquid sample containing an antigen complementary to the antibodies is introduced into one of the holes and the antigen diffuses through the gel in the manner described above so that a visible matrix is progressively formed. This normally takes the form of a disc concentric with the hole, one typical disc of this kind being indicated at 6. The diameter of the disc is measured to enable the concentration of antigen in the sample to be deduced.

There are several ways in which the plate may be used. In one method, a test sample of unknown strength is introduced into one of the holes 4 while several standard Samples, each of a known strength, are introduced into other holes. When the discs around the samples have reached suitably large sizes, their diameters are measured. Those resulting from the standard samples are plotted as points on a graph of diameter against strength. A line is drawn through those points and the strength of the test sample is assessed from the diameter of the matrix visible around the hole into which it was introduced. Using that method it may be possible to obtain useful results in a single day. In a somewhat similar method, which may lead to greater accuracy but may well take longer, the method is continued until the discs have reached their maximum diameters. This may take two days or even more. In another method, the plate is calibrated by the manufacturer and a table is provided showing the maximum diameters of the matrices that will be obtained with samples of given strengths.

Test plates of the kind described can be used by relatively unskilled people and without the need for complex or expensive measuring devices. In particular they enable doctors to carry out tests quickly and simply without the need to make use of equipment and expertise normally available only at a hospital.

The first of the known methods referred to above enabled measurements to be made with samples containing concentrations of antigens down to about 5 mg/l but the present invention readily enables measurements to be made with samples containing concentrations of antigens down to 0.5 mg/l, and in some cases the limit may be reduced to 0.15 or 0.2 mg/l. Consequently, many conditions that have hitherto been detectable and measurable only after reference to a hospital can now be detected and measured by a local doctor.

I claim:

1. A method of detecting the presence of the first of a pair of complementary matrix-forming agents in a sample, in which method the sample is applied to a test body comprising a gel in which there is present the second of said pair of complementary matrix-forming agents, said second agent being attached to particulate carrier material, said particulate carrier material being capable of movement within said gel, allowing said first agent to diffuse through the gel until it is incorporated in a light-scattering matrix of said first agent, said second agent and said particulate carrier material, the light-scattering properties of the matrix differing from those of the test body, and using a change in the light scattering properties resulting from the formation of the matrix, to detect the presence of the matrix and consequently the presence of said first agent in the sample.

2. A method according to claim 1 in which one of the matrix-forming agents is an antibody and the other is an antigen.

3. A test body for use in carrying out a method for detecting the presence of the first of a pair of complementary matrix-forming agents in a sample comprising a gel in which there is present a second matrix-forming agent attached to particulate carrier material, said particulate carrier material being capable of movement within said gel, such that incorporation of the second matrix-forming agent and attached particles in a matrix with the first agent changes the light-scattering properties of the test body the light-scattering properties of the matrix differing from those of a test body in which no matrix has been formed.

4. A test body according to claim 3 in which the particulate carrier material comprises polystyrene particles.

5. A test body according to claim 4 and in which each particle is of about 100 nm in diameter.

6. A test body according to claim 3 in which the test body is in the shape of a lamina of uniform thickness with at least one hole or well in it into which a sample can be introduced.

7. A single stage test method for detecting the presence of the first of a pair of complementary matrix-forming agents in a sample, in which a single liquid, containing the sample, is applied to a test body comprising a gel in which there is present the second of said pair of complementary matrix-forming agents, said second agent being attached to particulate carrier material, said particulate carrier material being capable of movement within the gel, allowing said first agent (if present) to diffuse through the gel until it is incorporated in a light-scattering matrix, the light-scattering properties of the matrix differing from those of the test body, and using a change in the light-scattering properties resulting from the formation of the matrix, to detect the presence of the matrix and consequently the presence of said first agent in the sample.

8. A test method according to claim 7 in which the light scattering matrix is formed as a result of a chemical reaction involving only said first and said second agent.

9. A test method according to claim 7 in which no agents are removed from the test body prior to obtaining a result.

10. A test method according to claim 7 in which the test body is not washed prior to obtaining a result.

11. A method of detecting the presence of the first of a pair of complementary matrix-forming agents in a sample, in which method a sample is applied to a test body comprising a gel in which there is present the second of said pair of complementary matrix-forming agents, said second agent being attached to particulate carrier material, the particulate carrier material being capable of at least limited movement within a gel, allowing said first agent (if present) to diffuse through the gel until it is incorporated in a light-scattering matrix, the light-scattering properties of the matrix differing from those of the test body, the change in the light-scattering properties resulting from the formation of the matrix being visible to a human eye, so as to indicate the presence of the matrix and consequently the presence of said first agent in the sample.

12. A method of detecting the present of the first of a pair of complementary matrix-forming agents in a sample by means of a test body comprising a gel in which there is present the second of said pair of complementary matrix-forming agents, said second agent being attached to particulate carrier material, said particulate carrier material being .capable of movement within the gel, said method comprising applying said sample to a first discrete area of a test body and allowing said first agent (if present) to diffuse through the gel until it is incorporated in a second discrete area comprising a light-scattering matrix, the light-scattering properties of the matrix differing from those of the test body, and using a change in the light-scattering properties resulting from the formation of the matrix to detect the presence of the matrix and consequently the presence of said first agent in the sample.

13. A method of detecting the presence of the first of a pair of complementary matrix—forming agents in a sample according to claim 12, in which the method further comprises a measuring step, said measuring step comprising a measurement of a dimension of said second discrete area of light-scattering matrix.

14. A method according to claim 13 in which the sample is applied to a well in the test body.

15. A method according to claim 13 in which said second discrete area of light-scattering matrix has a substantially circular external periphery and the dimension measured is the diameter of the matrix.

16. A testbody according to claim 3 in which said particulate carrier material is colloidal.

17. A test body according to claim 3 in which the particulate carrier material is of transparent or translucent material.

18. A test body according to claim 3 in which the particulate carrier material has an opaque core.

19. A method of detecting the presence of the first of a pair of complementary matrix-forming agents in a sample, in which method said sample is applied to a test body comprising a gel, said gel containing the second of said pair of complementary matrix-forming agents, said gel being provided with a plurality of particulate carrier material, said particulate carrier material being spaced from one another in said gel and said second agent being attached to said particulate carrier material, wherein said first agent (if present) is allowed to diffuse through said gel, said first agent (if present) and said second agent reacting to form a light-scattering matrix, the light-scattering properties of said matrix differing from those of said gel and said spacing of said particulate carrier material being altered in forming said matrix and using a change in the light-scattering properties resulting from the formation of the matrix to detect the presence of the matrix and consequently the presence of said first agent in the sample.

20. A method according to claim 19 in which one of said first and said second agents is an antibody and the other is an antigen.

21. A test body for use in a method of detecting the presence of a first of a pair of complementary matrix-forming agents in a sample, said test body comprising a gel, said gel containing the second of said pair of matrix-forming agents attached to particulate carriers, said particulate carriers being capable of migrating in said gel, the arrangement being such that incorporation of said second matrix-forming agent and attached particulate carriers in a matrix with said first agent binding to said second agent changes the light-scattering properties of said gel by altering the spacing of said particulate carriers, said light-scattering properties of said matrix differing from those of said gel in which no matrix has been formed.

* * * * *